(12) United States Patent
Santini

(10) Patent No.: US 11,766,353 B2
(45) Date of Patent: Sep. 26, 2023

(54) INFLATABLE THERAPY BAND WITH POCKETS

(71) Applicant: Brian Santini, Pompton Plains, NJ (US)

(72) Inventor: Brian Santini, Pompton Plains, NJ (US)

( * ) Notice: Subject to any disclaimer, the term of this patent is extended or adjusted under 35 U.S.C. 154(b) by 441 days.

(21) Appl. No.: 17/082,089

(22) Filed: Oct. 28, 2020

(65) Prior Publication Data

US 2022/0125628 A1 Apr. 28, 2022

(51) Int. Cl.
*A61F 7/10* (2006.01)
*A61F 5/34* (2006.01)
*A61F 7/02* (2006.01)

(52) U.S. Cl.
CPC .......... *A61F 7/10* (2013.01); *A61F 5/34* (2013.01); *A61F 7/02* (2013.01); *A61F 2007/023* (2013.01); *A61F 2007/108* (2013.01)

(58) Field of Classification Search
CPC ...... A61F 2007/0007; A61F 2007/0091; A61F 2007/0204; A61F 2007/0207; A61F 2007/0225; A61F 2007/0228; A61F 2007/023; A61F 2007/0231; A61F 2007/0242; A61F 2007/108; A61F 5/34; A61F 7/02; A61F 7/10
See application file for complete search history.

(56) References Cited

U.S. PATENT DOCUMENTS

| | | | |
|---|---|---|---|
| 3,717,145 A | 2/1973 | Berndt et al. | |
| 4,628,918 A | 12/1986 | Johnson, Jr. | |
| 5,193,549 A | 3/1993 | Bellin et al. | |
| 5,310,400 A | 5/1994 | Rogers et al. | |
| 5,372,575 A | 12/1994 | Sebastian | |
| 5,407,421 A * | 4/1995 | Goldsmith | A61F 7/02 602/5 |
| 8,535,253 B2 | 9/2013 | Vess | |
| 8,628,488 B2 | 1/2014 | Serola | |
| 9,789,006 B2 | 10/2017 | Joyner | |
| 10,610,661 B2 | 4/2020 | Nofzinger | |
| 2017/0209333 A1* | 7/2017 | Shoup | A61M 21/02 |
| 2020/0375795 A1* | 12/2020 | Fulbrook | A61F 7/02 |

* cited by examiner

*Primary Examiner* — Tigist S Demie
(74) *Attorney, Agent, or Firm* — CRAMER PATENT & DESIGN, PLLC; Aaron R. Cramer

(57) ABSTRACT

An inflatable therapy band with pocket comprises a circular band configured to removably be secured about a head. The band comprises four pockets for an ice pack and four inflatable air bladders. The pocket for the ice packets and air bladders alternate about the length of the band. An air pump is provided on the band which is in pneumatic communication with the air bladders.

17 Claims, 5 Drawing Sheets

INFLATABLE THERAPY BAND WITH POCKETS

RELATED APPLICATIONS

Non-applicable.

FIELD OF THE INVENTION

The present invention relates generally to a therapy band and more specifically to a therapy band with pockets.

BACKGROUND OF THE INVENTION

Many people suffer from body aches and pains, headaches, and other pain that is derived from a number of sources. Many people suffer from residual pain that began as a result of a previous injury that never completely heals or is easily aggravated. Others suffer from pain that stems from the stress and strain of daily work from lifting objects or remaining in a fixed position for long periods of time. Regardless of its origin, essential in relieving this pain is the application of heat or cold directly to the area, along with mild pressure.

However, due to the size of the heated or cooled temperature source, it can only contact one area of the body at a time. Additionally, the user must hold the temperature source and/or pressure, in position with a hand or hands, thus preventing the user from realizing a normal life that provides freedom of movement and use of their hands. Finally, should the user attempt to use the modified temperature source at night while sleeping, it is sure to become dislodged at the first toss or turn thereby rendering it ineffective. Accordingly, there exists a need for a means by which a source of relatively large hot or cold temperature sources can be secured using pressure against varying body locations in a manner that does not require holding by hands. The development of the inflatable temperature therapy band with pockets fulfills this need.

SUMMARY OF THE INVENTION

The principles of the present invention provide for an inflatable temperature therapy band which has a plurality of pockets each of which are secured by a flap, a retaining device which secures each of the flaps corresponding to each of the pockets, a pressurization port which connects a tube and a pressure bulb with a threaded fitting to inflate each of a plurality of inflatable bladders, and a pressure relief port which is manipulated to release pressure from the inflatable bladders which allows the inflatable temperature therapy band to be removed.

The pockets may be interconnected by the inflatable bladders that are physically connected to each of the pockets. The pockets may be pneumatically connected by an interconnecting tube, thereby sharing an interior space between each one of the inflatable bladders. The diameter of each of the interconnected pockets and each of the inflatable bladders may be different to accommodate different sized body parts. Each of the pockets are filled with a plurality of freezable modules prior to placement on the user. The freezable modules may be prepared before use by placing them in a freezer. The freezable modules may be filled with a freezable liquid selected from the group consisting of water, hydroxyethyl cellulose, sodium polyacrylate, or vinyl-coated silica gel.

Each of the pockets may be filled with a plurality of heatable modules prior to placement on the user. The heatable modules may be prepared before use by placing them in an oven or a microwave oven. The heatable modules may be made of material selected from the group consisting of water, one or more grains, wheat, buckwheat, flax seed, or sand. Four of the pockets may be sequentially connected to each of the four inflatable bladders, with the interconnecting tube routed over the pockets to each one of the inflatable bladders.

The retaining device may be selected from the group consisting of a snap, a hook-and-loop-type fastener, or a zipper. The tube and the pressure bulb may be removed during use for ease of movement from removing the tube and the pressure bulb. The inflatable temperature therapy band may apply pressure and heat to one or more parts of the body without holding them in place. The inflatable temperature therapy band may apply pressure and cold to one or more parts of a user's body without holding them in place.

The inflatable temperature therapy band may be pressurized so that the inflatable temperature therapy band remains in place on a desired body part. The inflatable temperature therapy band may also comprise a pressure relief valve to vent the pressurized tube so that the tube and the pressure bulb is removed. The inflatable temperature therapy band may be adapted to be positioned in a horizontal position around the forehead and the back of the head of a user to treat a headache, a migraine headache, or sinus pain.

The inflatable temperature therapy band may be used in a vertical position around the jaw and the top of the head of the user to treat dental pain or in a vertical position around the jaw and the top of the head of the user to treat an earache.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
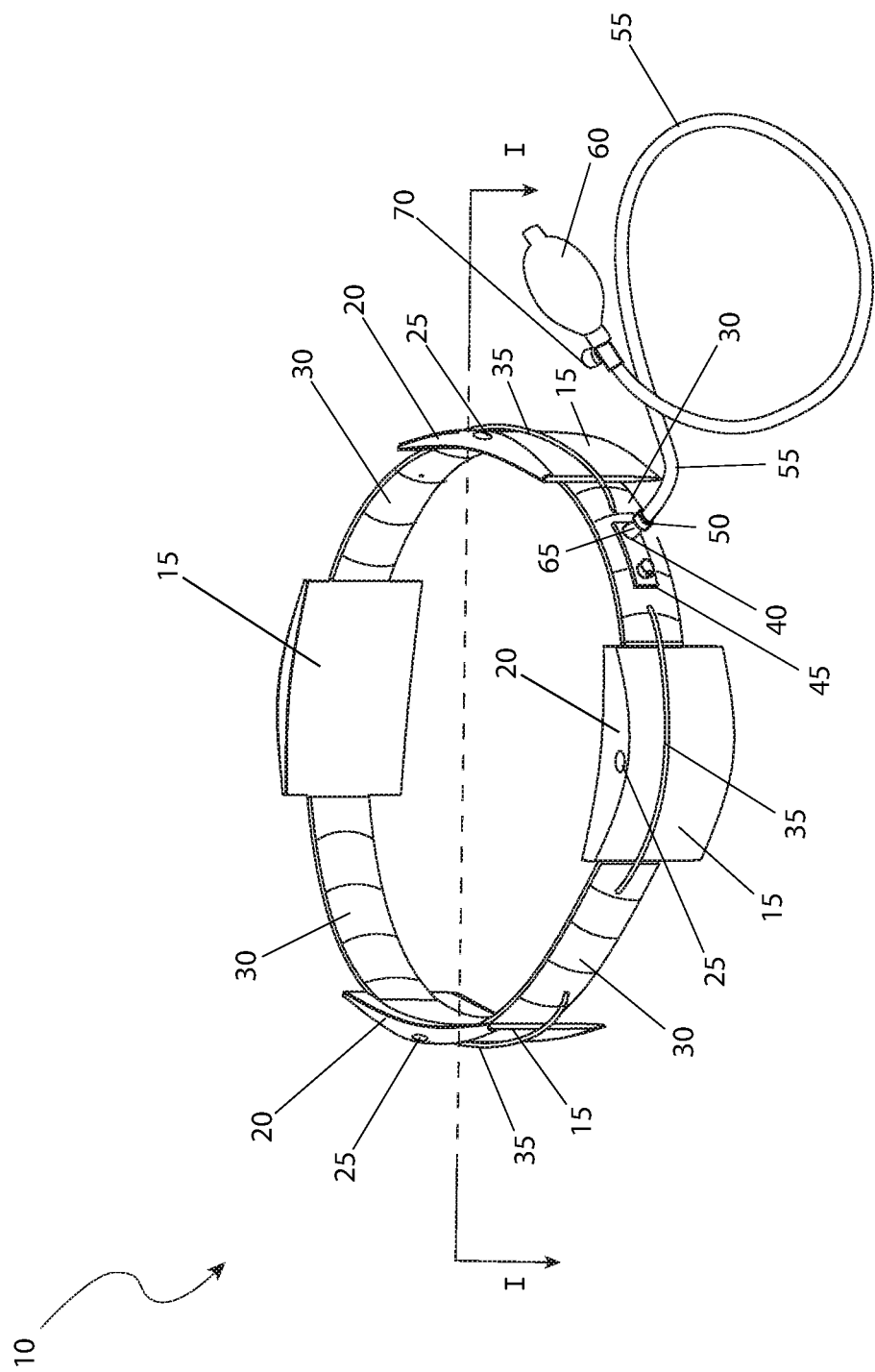
FIG. 1 is a perspective view of the inflatable temperature therapy band, according to the preferred embodiment of the present invention.

DESCRIPTIVE KEY 10 inflatable temperature therapy band
15 pocket
20 flap
25 retaining device
30 inflatable bladder
35 interconnecting tube 40 pressurization port
45 pressure relief port
50 threaded fitting
55 tube
60 pressure bulb
65 check valve
70 pressure relief valve
75 head
80 forehead
85 back of head
90 jaw
95 top of head
100 freezable module
105 heatable module
110 elbow
115 arm
120 wrist
125 forearm
130 upper arm
135 knee
140 leg
145 ankle
150 calf
155 thigh
160 force application path "f"

DESCRIPTION OF THE PREFERRED EMBODIMENTS

The best mode for carrying out the invention is presented in terms of its preferred embodiment, herein depicted within FIGS. 1 through 5. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope. All of the implementations described below are exemplary implementations provided to enable persons skilled in the art to make or use the embodiments of the disclosure and are not intended to limit the scope of the disclosure, which is defined by the claims.

The terms "a" and "an" herein do not denote a limitation of quantity, but rather denote the presence of at least one (1) of the referenced items.

1. Detailed Description of the Figures

Referring now to FIG. 1, a perspective view of the inflatable temperature therapy band 10, according to the preferred embodiment of the present invention is disclosed. The inflatable temperature therapy band 10 (herein also described as the "device") 10, is a pain relief apparatus that applies pressure along with hot or cold temperatures to varying parts of the body without the necessity to hold them in place. The invention includes multiple pockets 15, each pocket 15 is secured by a flap 20 along with a retaining device 25 such as a snap (as shown), hook-and-loop-type fastener (Velcro®), zipper, or the like. The exact type of retaining device 25, size of the pockets 15, or quantity of the pockets 15 is not intended to be a limiting factor of the present invention. The pockets 15 are interconnected by a series of inflatable bladders 30 that physically connect to each pocket 15, and are pneumatically connected by an interconnecting tube 35, thereby sharing a common interior space from each inflatable bladder 30 to the next inflatable bladder 30. The overall diameter afforded by the interconnected pockets 15 and inflatable bladders 30 would vary by model for different sizes of body parts. A large version would be used to go around a user's head or thigh area, medium ones around knees or upper arm areas while the smallest versions would be used for elbows, forearms and wrist areas. Larger and smaller versions would be used for adults and children respectively as well.

The device 10 is provided with a pressurization port 40 and pressure relief port 45. The pressurization port 40 connects via threaded fitting 50 to a tube 55 and a pressure bulb 60 to inflate the inflatable bladders 30. Once the device 10 is pressurized to a point that said device 10 remains in place on the desired body part, a pressure relief valve 70 can vent the pressurized tube 55, and then the tube 55 and the pressure bulb 60 can be removed. Pressure is maintained by a check valve 65. When the device 10 is to be removed, a pressure relief port 45 is manipulated to release the pressure allowing the device 10 to be removed. The removal of the tube 55 and pressure bulb 60 during use is viewed to allow streamlined activities, movement, and even sleeping without having to deal with the cumbersome nature of the tube 55 and pressure bulb 60.

Figure 2:
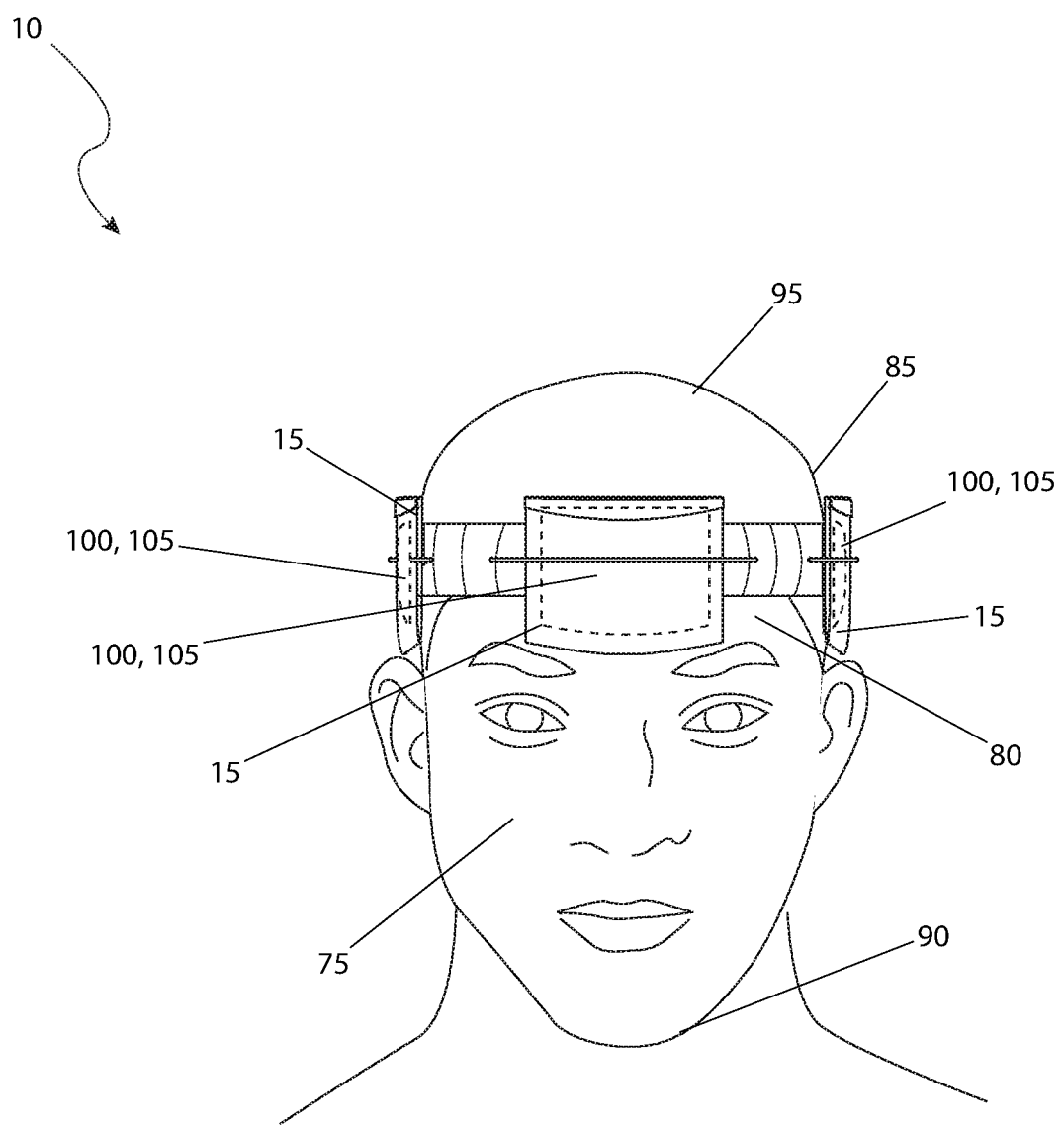
FIG. 2 is a perspective view of the inflatable temperature therapy band, shown in an installed state on a head, according to the preferred embodiment of the present invention.

Referring next to FIG. 2, a device 10, shown in an installed state on a head 75, according to the preferred embodiment of the present invention is depicted. The device 10 is depicted in a horizontal position around the forehead 80 and the back of the head 85 as would be appropriate for a headache, migraine headache, sinus pain or the like. It is envisioned that the invention could also be used in a vertical position around the jaw 90 and the top of head 95 as would be appropriate for dental pain, earaches or the like. Prior to placement on the head 75 area, each of the pockets 15 are filled with freezable modules 100 or heatable modules 105 (both shown with dashed lines due to their hidden nature). The freezable modules 100 are envisioned to be filled with a freezable liquid mixture such as water, hydroxyethyl cellulose (Cellosize™), sodium polyacrylate, or vinyl-coated silica gel. The heatable modules 105 may be made of water, grains such as wheat, buckwheat or flax seed, sand or the like. The exact composition and materials of construction of the freezable modules 100 and the heatable modules 105 are not intended to be a limiting factor of the present invention. The freezable modules 100 would be prepared before use by placing it in a freezer. The heatable modules 105 would be prepared before use by placing it in an oven or microwave.

Figure 3:
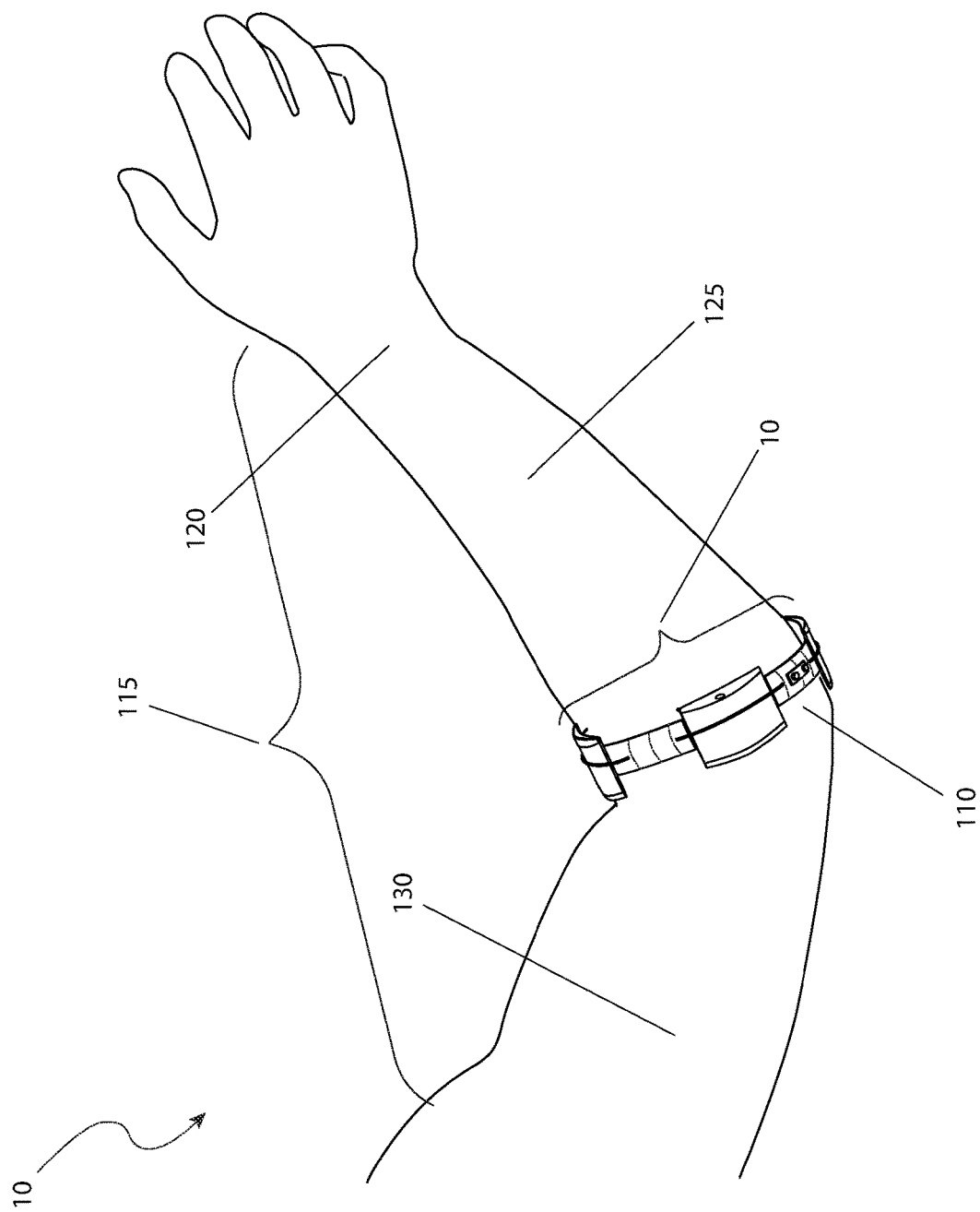
FIG. 3 is a perspective view of the inflatable temperature therapy band, shown in an installed state on an elbow, according to the preferred embodiment of the present invention.

Referring now to FIG. 3, a perspective view of the device 10, shown in an installed state on an elbow 110, according to the preferred embodiment of the present invention is shown. The device 10 is positioned such that maximum hot or cold temperatures can be transferred to the elbow 110. While the positioning of the device 10 is on the elbow 110, other areas of the arm 115 such as the wrist 120, the forearm 125, or the upper arm 130 may also be targeted by simply positioning the device 10 and reinflating the device 10 using the tube 55 and the pressure bulb 60 (both of which were previously described in FIG. 1).

Figure 4:
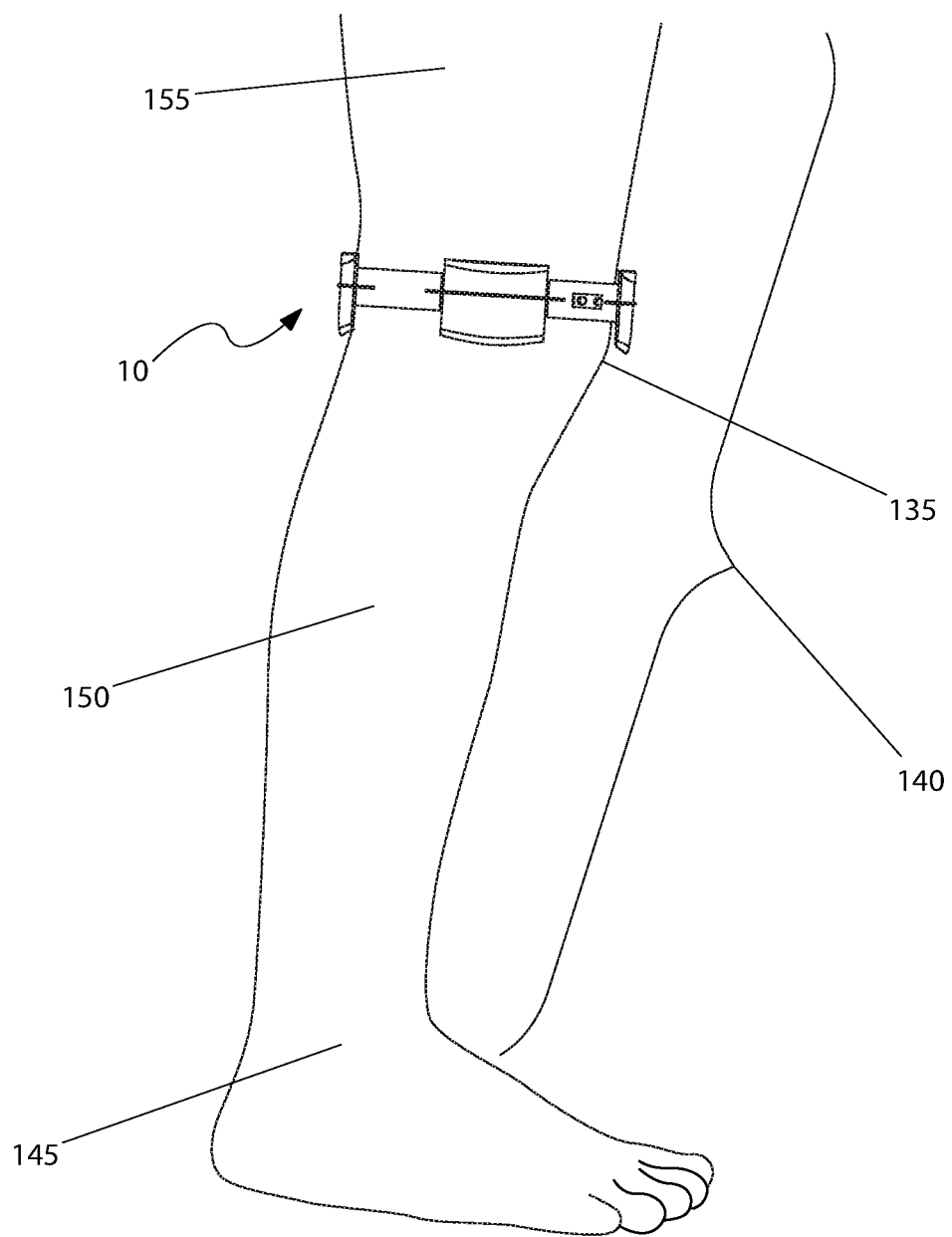
FIG. 4 is a perspective view of the inflatable temperature therapy band, shown in an installed state on a knee, according to the preferred embodiment of the present invention.

Referring next to FIG. 4, a device 10, shown in an installed state on a knee 135, according to the preferred embodiment of the present invention is disclosed. The device 10 is positioned such that maximum hot or cold temperatures can be transferred to the knee 135. While the positioning of the device 10 is on the knee 135, other areas of the leg 140 such as the ankle 145, the calf 150, or the thigh 155 may also be targeted by simply positioning the device 10 and reinflating the device 10 using the tube 55 and the pressure bulb 60 (both of which were previously described in FIG. 1).

Figure 5:
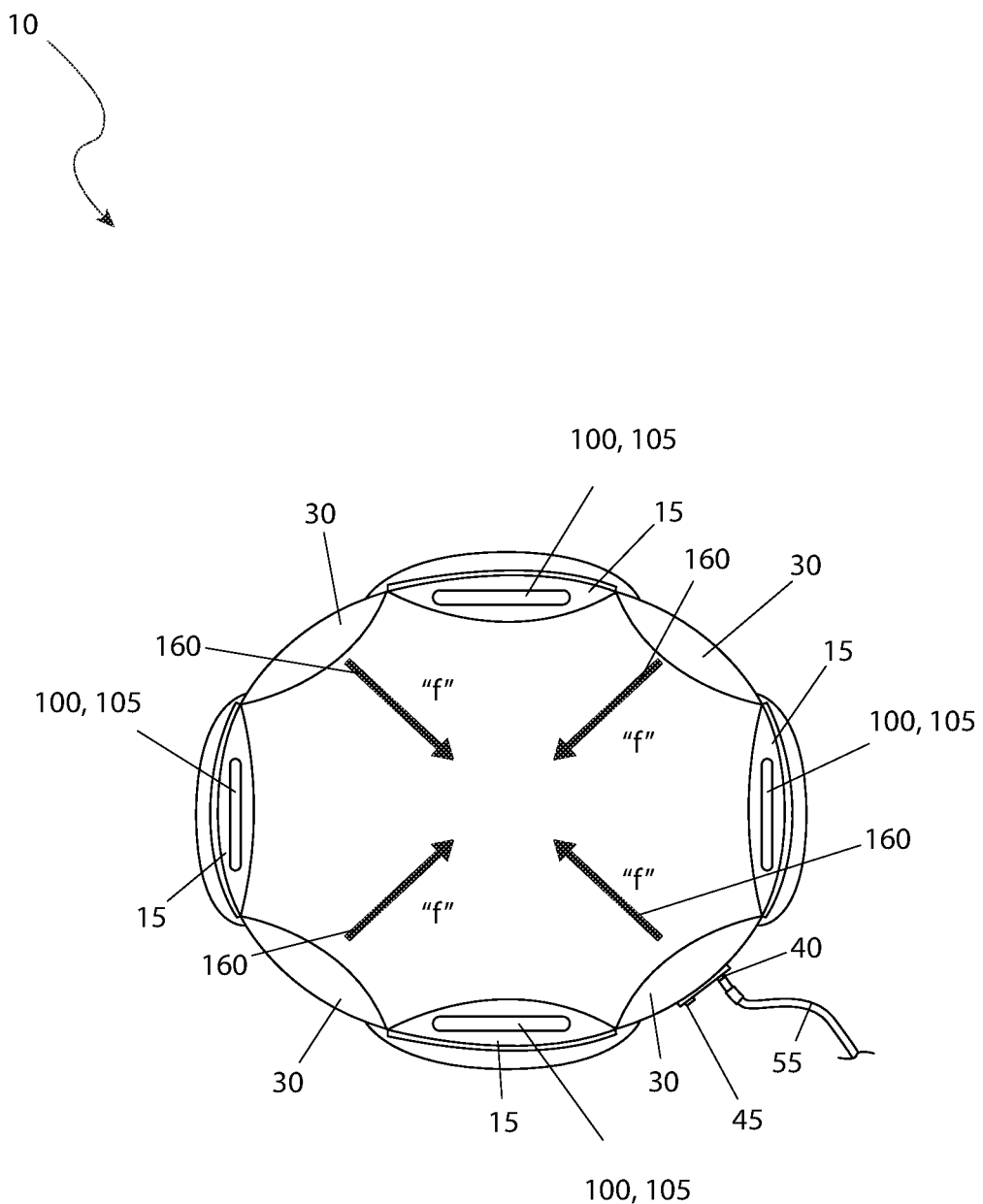
FIG. 5 is a sectional view of the inflatable temperature therapy band, as seen along a line I-I, as shown in FIG. 1, according to the preferred embodiment of the present invention.

Referring finally to FIG. 5, a sectional view of the device 10, as seen along a line I-I, as shown in FIG. 1, according to the preferred embodiment of the present invention is depicted. This view clearly depicts the circular arrangement of the device 10. Each of the four (4) pockets 15 are sequentially connected to each of the four (4) inflatable bladders 30, with the interconnecting tube 35 routed over the pockets 15 to each inflatable bladder 30. As the inflatable bladders 30 are inflated while connected to the tube 55 via the pressurization port 40, they exert a force application path "f" 160, against the head 75 (as shown in FIG. 2), the elbow 110 (as shown in FIG. 3), the knee 135 (as shown in FIG. 4) or any other body part that can be encircled by the device 10. It is envisioned that not only the cold temperatures from the freezable modules 100, or the warm temperatures from the heatable modules 105 will bring comfort, but also the pressure itself.

2. Operation of the Preferred Embodiment

The preferred embodiment of the present invention can be utilized by the common user in a simple and effortless manner with little or no training. It is envisioned that the device 10 would be constructed in general accordance with FIG. 1 through FIG. 5. The user would procure the device 10 from conventional procurement channels such as discount stores, department stores, drug stores, hospital supply stores, mail order and internet supply houses and the like. Special attention would be paid to the overall size of the device 10 with respect to the diameter of the body part in which it is intended to be used.

After procurement and prior to utilization, the device 10 would be prepared in the following manner: depending on the temperature of treatment desired, the user would place the freezable modules 100 into a freezer for a suitable period of time until frozen or place the heatable modules 105 into an oven or microwave until suitably warmed; the user would select the proper size of the device 10 with respect to the diameter of the body part in which it is intended to be used, such as for the head 75, the elbow 110, the wrist 120, the forearm 125, the upper arm 130, the knee 135, the ankle 145, the calf 150, or the thigh 155; and the freezable modules 100 or the heatable modules 105 would be placed into the pockets 15 of the device 10; the flap 20 closed and secured with the retaining device 25. At this point in time, the device 10 is ready for utilization.

During utilization of the device 10, the following procedure would be initiated: the device 10 is slide over the desired body part as described above; the tube 55 and the pressure bulb 60 is attached to the pressurization port 40 via the threaded fitting 50; the pressure bulb 60 is then manipulated to provide the desired amount of pressure along the force application path "f" 160 to not only hold the device 10 in place, but to provide comfort as well; the tube 55 and the pressure bulb 60 are then removed by venting the tube 55 via the pressure relief valve 70 with the air pressure being held inside of the inflatable bladders 30 via the check valve 65; the hot or cold temperatures from the heatable modules 105 or the freezable modules 100 respectively are then given adequate time for pain relief.

After use of the device 10, it is removed via manipulation of the pressure relief port 45 to release the air pressure; the device 10 is then slid off of the body part; the freezable modules 100 or the heatable modules 105 are removed; and the device 10 is stored until needed again in a circular repeating manner.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. An inflatable temperature therapy band, comprising:
a plurality of pockets each secured by a flap;
a retaining device securing each of the flaps corresponding to each of the pockets;
a pressurization port connecting a tube and a pressure bulb with a threaded fitting to inflate each of a plurality of inflatable bladders;
a pressure relief port is configured to be manipulated to release pressure from the inflatable bladders allowing the inflatable temperature therapy band to be removed; and,
wherein four of the pockets are sequentially connected to each of a four inflatable bladders, with an interconnecting tube routed over the pockets to each one of the inflatable bladders.

2. The inflatable temperature therapy band, according to claim 1, wherein the pockets are interconnected by the inflatable bladders that are physically connected to each of the pockets.

3. The inflatable temperature therapy band, according to claim 2, wherein the pockets are pneumatically connected by an interconnecting tube, thereby sharing an interior space between each one of the inflatable bladders.

4. The inflatable temperature therapy band, according to claim 3, wherein the diameter of each of the interconnected pockets and each of the inflatable bladders are different to accommodate different sized body parts.

5. The inflatable temperature therapy band, according to claim 4, wherein each of the pockets are filled with a plurality of freezable modules.

6. The inflatable temperature therapy band, according to claim 5, wherein the freezable modules are configured to be placed in a freezer.

7. The inflatable temperature therapy band, according to claim 5, wherein the freezable modules are filled with a freezable liquid selected from the group consisting of water, hydroxyethyl cellulose, sodium polyacrylate, or vinyl-coated silica gel.

8. The inflatable temperature therapy band, according to claim 1, wherein each of the pockets are filled with a plurality of heatable modules.

9. The inflatable temperature therapy band, according to claim 8, wherein the heatable modules are configured to be placed in an oven or a microwave oven.

10. The inflatable temperature therapy band, according to claim 8, wherein the heatable modules are made of material selected from the group consisting of water, one or more grains, wheat, buckwheat, flax seed, or sand.

11. The inflatable temperature therapy band, according to claim 1, wherein the retaining device is selected from the group consisting of a snap, a hook-and-loop-type fastener, or a zipper.

12. The inflatable temperature therapy band, according to claim 1, wherein the tube and the pressure bulb are configured to be removed during use for ease of movement from removing the tube and the pressure bulb.

13. The inflatable temperature therapy band, according to claim 1, wherein the inflatable temperature therapy band applies pressure and heat to one or more parts of the body without holding them in place.

14. The inflatable temperature therapy band, according to claim 1, wherein the inflatable temperature therapy band applies pressure and cold to one or more parts of a user's body without holding them in place.

15. The inflatable temperature therapy band, according to claim 1, wherein the inflatable temperature therapy band is pressurized so that the inflatable temperature therapy band remains in place on a desired body part.

16. The inflatable temperature therapy band, according to claim 15, further comprising a pressure relief valve to vent the pressurized tube so that the tube and the pressure bulb is removed.

17. The inflatable temperature therapy band, according to claim 1, wherein the inflatable temperature therapy band is adapted to be positioned in a horizontal position around the forehead and the back of the head of a user to treat a headache, a migraine headache, or sinus pain.

* * * * *